US00PP10247P

United States Patent [19]

Brown

[11] Patent Number: Plant 10,247

[45] Date of Patent: Feb. 17, 1998

[54] AGLAONEMA PLANT NAMED "STARS"

[75] Inventor: B. Frank Brown, Valkaria, Fla.

[73] Assignee: Sunshine Foliage World, Zolfo Springs, Fla.

[21] Appl. No.: 754,304

[22] Filed: Nov. 21, 1996

[51] Int. Cl.[6] ..... A01H 5/00

[52] U.S. Cl. ..... Plt./88.1

[58] Field of Search ..... Plt./88.1

*Primary Examiner*—James R. Feyrer

*Attorney, Agent, or Firm*—C. A. Whealy

[57] ABSTRACT

A new and distinct cultivar of Aglaonema named 'Stars' particularly characterized by its dark green leaves marked with dark silver-green blotches and white yellow-green speckles and its relatively short, well-branched and dense growth habit.

3 Drawing Sheets

The present invention relates to a new and distinct cultivar of Aglaonema plant, botanically known as *Algaonema hybrida*, and hereinafter referred to by the cultivar name Stars.

The new cultivar is a product of a planned breeding program conducted by the inventor in Valkaria, Fla. The new cultivar originated from a cross made by the inventor in August, 1986, between the nonpatented *Aglaonema costatum* var. maculatum as the female, or seed, parent with the species *Aglaonema brevispathum*. The cultivar Stars was discovered and selected by the inventor in September, 1987, as a plant within the progeny of the stated cross in a controlled environment in Valkaria, Fla.

Asexual propagation of the new cultivar at Valkaria, Fla., has shown that the unique features of this new Aglaonema plant are stable and reproduced true to type in successive generations of asexual propagation.

The new Aglaonema has not been observed under all possible environmental conditions. The phenotype may vary somewhat with variations in environment such as temperature, light intensity and fertilizer rate, without, however, any variance in genotype. The following observations, measurements and comparisons describe plants grown in Zolfo Springs, Fla., under a polypropylene-covered shadehouse and conditions which closely approximate those used in horticultural practice.

The following traits have been repeatedly observed and are determined to be the unique characteristics of 'Stars'. These characteristics in combination distinguish 'Stars' as a new and distinct cultivar:

1. Plants of the new Aglanonema are freely branching, relatively short and spreading in growth habit.

2. Plants of the new Aglaonema have numerous intermediate-sized leaves, giving the plant a dense and bushy appearance.

3. The abaxial leaf surfaces of the new Aglaonema are dark green in base color with large dark silver green blotches. The leaves are speckled with white or yellow-green spots which are visible from both sides of the leaf. The midrib is white and tinged with yellow-green.

Perhaps the closest commercial comparison to the new Aglaonema is *Dieffenbachia×bausei* which has a similar leaf color pattern and shape. However plants of *Dieffenbachia× bausei* are less freely branching, grow much taller, and lack the durability which is characteristic of the genus Aglaonema.

The accompanying colored photographs illustrate the overall appearance of the new cultivar, showing the colors as true as it is reasonably possible to obtain in colored reproduction of this type.

The first photograph comprises a top perspective view of a typical single plant of 'Stars' in a 26-cm container about 18 months after planting a single four-leaf cutting.

The second photograph comprises a close-up view of the abaxial surface of a mature leaf and illustrates the detail of the leaf color pattern.

The third photograph comprises a close-up view of the adaxial surface of a mature leaf and illustrates the detail of the leaf color pattern.

Leaf colors in the photographs may appear different from the actual colors due to light reflectance.

In the following description, color references are made to The Royal Horticultural Society Colour Chart except where general terms of ordinary dictionary significance are used.

Botanical classification: *Aglaonema hybrida* cultivar 'Stars'.

Parentage:

*Seed or female parent.*—*Aglaonema costatum* var. maculatum (not patented).

*Pollen or male parent.*—*Aglaonema brevispathum.*

Propagation: Asexual propagation by division or tissue culture.

Plant description:

*Plant shape.*—Relatively compact and wide, outwardly spreading, freely branching, dense and symmetrical.

*Growth habit.*—Relatively erect when young, becoming more outwardly spreading as leaves develop.

*Plant size.*—Height: Soil surface to top of leaf canopy: Approximately 35 to 48 cm. Soil surface to junction of the petioles of the last two unrolled leaves: Approximately 12 to 16 cm. Width: Approximately 74 to 80 cm.

*Root description.*—Thick white roots with fine laterals.

*Stem description.*—Upright. Diameter, 5 cm above the soil surface: Approximately 1.4 to 1.7 cm. Internode length, 3 cm above the soil surface: Approximately 0.9 to 2.2 cm. Color: Greener than 161C/161D with areas of 146A.

*Petiole description.*—The following description is based on the fourth expanded leaf from the apex. Growth pattern: The petiole has fleshy edges extending from the midrib that are referred to as wings. Wings extend from the base of the petiole to approximately 6.6 to 7.5 cm below the base of the leaf. The wings are about 4 to 7 mm wide midway from the petiole base to the wing apex. The wing apex is acute. The petiole follows the stem axis but diverges from the axis about 15 to 18 cm from the leaf base, forming a horizontal distance from the vertical axis of the stem to the leaf base of approximately 5 to 7.5 cm. Dimensions: The petiole is straight from its base to the tip of the wings, and often curved between the tip of the wings and the base of the leaf. The petiole is approximately 5 to 6 mm in diameter midway between the wing apex and the base of the leaf. The petiole is approximately 17.3 to 19.8 cm in length from its base to the base of the leaf. Color: Petiole wings: 137A with small speckles of 138A. Midrib: Darker than 137A.

*Axillary breaks.*—There are approximately 12 axillary breaks with at least one leaf expanded. First leaves will show true color and color pattern.

*Leaf description.*—Growth Pattern: The leaf is ovate with an acute apex and an obtuse base. The margin is entire. The leaf is oriented parallel to the stem axis at the time of full unrolling, changing to approximately 40 degrees from vertical stem axis as more leaves unroll about it. The midrib is straight. The leaf blade is somewhat wavy, and often distinctly puckered along the midrib. The leaf margin is often somewhat wavy. Dimensions: For the pot size and growing time indicated, the largest leaves are approximately 24.5 to 30.9 cm long and approximately 10.7 to 13.3 cm wide. Average sized leaves are approximately 22.1 to 24.2 cm long and approximately 9.6 to 10.5 cm wide. The leaf blade is relatively thin with a leathery texture and a matte to slightly glossy surface. Midrib: The midrib is thick and prominent, recessed on the abaxial leaf surface and prominent on the adaxial surface. Primary veins: The primary veins are sunken into the abaxial surface and slightly prominent on the adaxial surface. The primary veins are the same color as the tissue surrounding them. The leaf blade is convex between the primary veins. Color pattern: The abaxial leaf surfaces are dark green in base color. Large prominent dark silver-green blotches occupy much of the central leaf surface. The leaf blade is randomly speckled with small white and yellow-green spots which are visible from both sides of the leaf. The number of white and yellow-green speckles is greatest on juvenile growth, and considerably reduced on larger more mature growth. The midrib is white, and often tinged with yellow-green. The adaxial leaf surface is medium green with pale silver green chevrons which follow the primary veins. The midrib is medium green. Small white or yellow-green speckles randomly dot the entire leaf surface, and are more abundant on the adaxial surface than on the abaxial surface. Color: Mature leaf, abaxial surface: Base color: 147A with dark silver-green blotches which are darker than 147B. White and yellow-green speckles/spots of 150D/155A. Midrib — 155D/150D. Mature leaf, adaxial surface: Base color: Darker than 137C with, pale silver-green chevrons of 138B. White and yellow-green speckles of 145D/150D. Midrib: 137C. Newly opened leaf, abaxial surface: Base color: Greener than 147A, with silver-green blotches of 147B. White and yellow-green speckles of 145D/150D. Midrib: 155D. Newly opened leaf, adaxial surface: Base color: 147B with pale silver-green chevrons of 138B. White and yellow-green speckles of 145D/150D. Midrib: Lighter than 147B/147C.

*Inflorescence.*—Typical of Aglaonema, no commercial significance.

General Observations

Aglaonema 'Stars' is a freely branching, relatively short-growing variety having dark green leaves prominently marked with dark silver-green blotches and distinctive white and yellow-green speckles which are visible from both sides of the leaf. These characteristics in combination make 'Stars' a unique and distinct new cultivar.

It is claimed:

1. A new and distinct cultivar of Aglaonema plant named 'Stars', as illustrated and described.

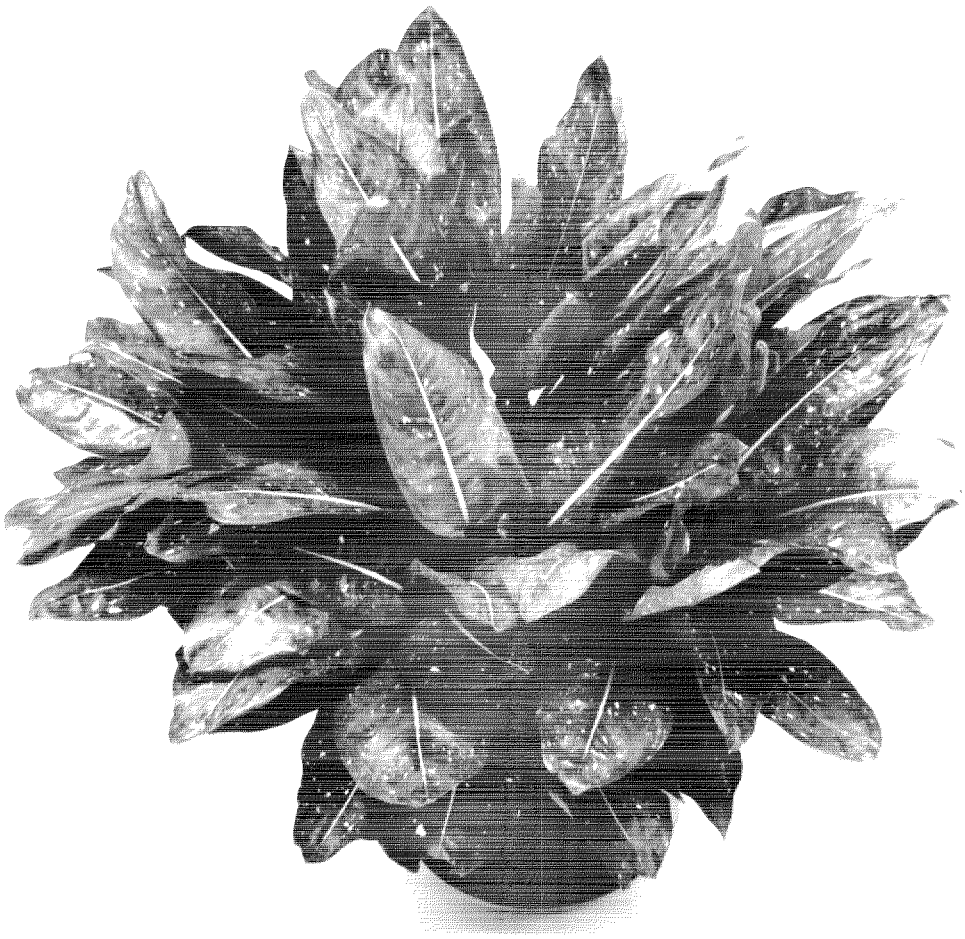

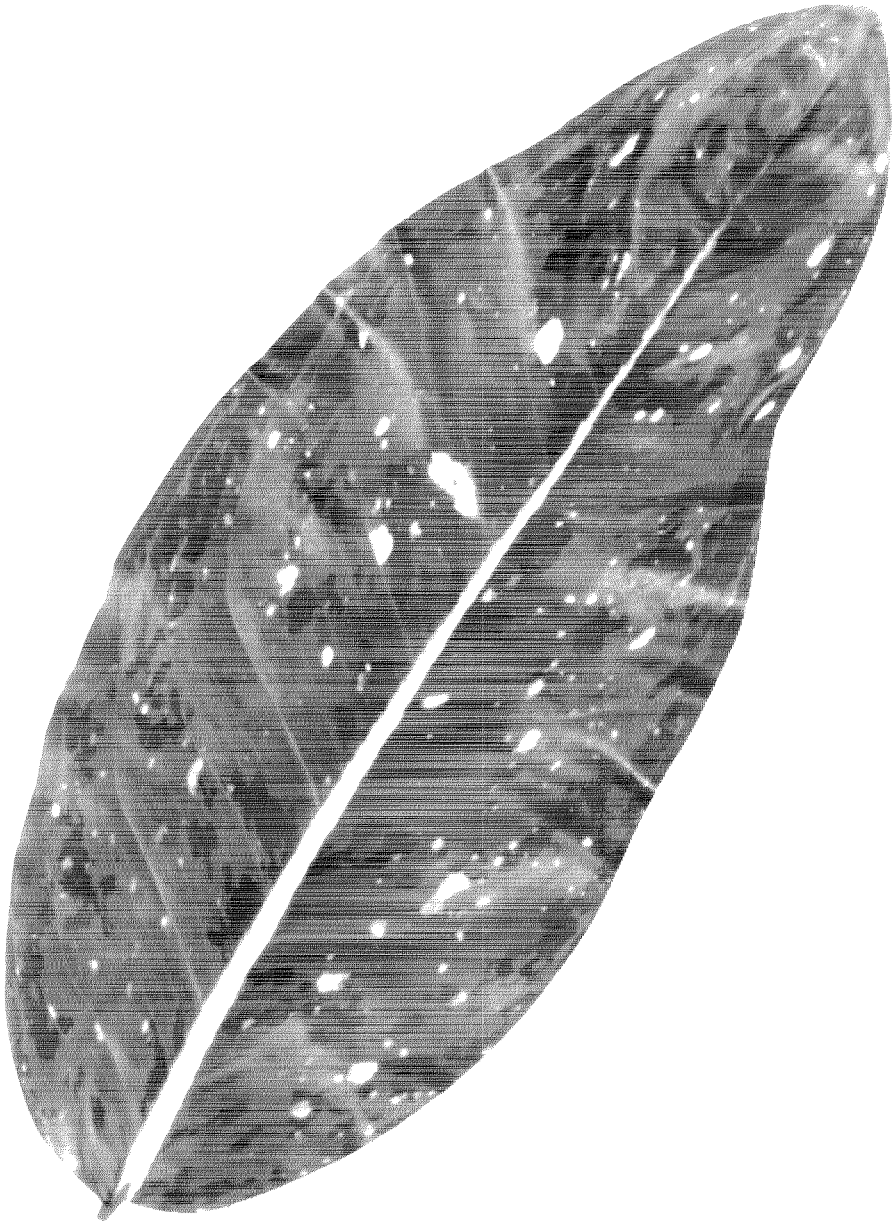

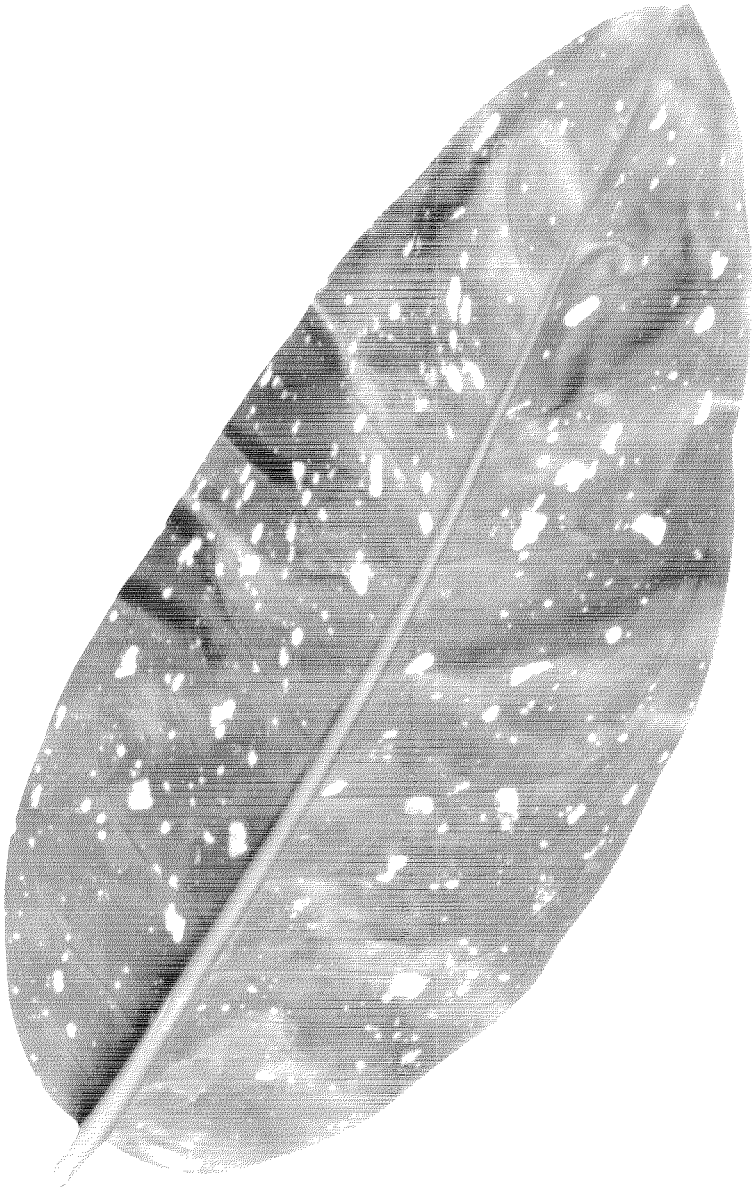

* * * * *